United States Patent [19]

Schnee et al.

[11] 4,031,064

[45] June 21, 1977

[54] AMINOPLAST CURING AGENTS

[75] Inventors: Karl Schnee, Maintal; Dieter Tichy, Frankfurt am Main; Steffen Piesch, Oberursel, all of Germany

[73] Assignee: Cassella Farbwerke Mainkur Aktiengesellschaft, Germany

[22] Filed: Apr. 18, 1975

[21] Appl. No.: 569,408

[30] Foreign Application Priority Data

Apr. 20, 1974 Germany .......................... 2419124

[52] U.S. Cl. ..................... 260/67.6 R; 260/67.6 C; 260/67.7; 260/67.8; 260/246 B; 260/247.1 R; 260/247.2 R; 260/247.2 A; 260/269; 260/313.1; 260/518 R; 260/518 A; 260/521 N; 260/521 H; 260/534 R; 260/534 M; 260/534 S

[51] Int. Cl.² .......................................... C08G 12/26
[58] Field of Search ................. 260/67.6 R, 67.6 C, 260/67.7, 67.8, 518 R, 518 A, 519, 521 N, 521 H, 534 R, 534 M, 534 S, 246 B, 247.2 R, 247.2 A, 247.1, 269, 313.1

[56] References Cited

UNITED STATES PATENTS 3,624,246  11/1971  Deuzerman .................. 260/67.6 R

*Primary Examiner*—J. Ziegler
*Attorney, Agent, or Firm*—Connolly and Hutz

[57] ABSTRACT

Maleamic and fumaramic acids and certain of their derivatives make very good curing agents for converting aminoplast condensates to cured resins.

12 Claims, No Drawings

AMINOPLAST CURING AGENTS

The invention relates to the curing of aminoplast condensation products with maleamic acid or fumaramic acid or their water-soluble salts.

Aminoplasts are polycondensation products obtained by the reaction of a carbonyl compound with a constituent containing amino, imino, or amide groups (see Ullmanns Encyklopadie der Technischen Chemie, Fourth Edition, Vol. 7 (1974), pages 403–424). The technically most important aminoplasts are prepared by the condensation of formaldehyde with urea or melamine. In the preparation, the condensation is carried out only so far that the reaction products remain still soluble and meltable. When this state is reached, the condensation is discontinued, as by cooling and adjusting the pH to a weakly alkaline value.

The products thus prepared (aminoplast condensates) are utilized in the form of their aqueous solutions, particularly as impregnants for the molded laminated plastics industry and for the surface finishing of chip boards as well as for the manufacture of molded plastics.

In impregnant use paper or textiles are impregnated with solutions of the uncured aminoplast condensation product and then laminated to base sheets and cured as by hot pressing. This procedure is used for the preparation of decorative laminated sheets as well as for the coating of wood materials, primarily wood-chip boards and wood fiber boards (see Ullmann loc. cit., pages 417–418).

For the preparation of molded plastics, the uncured aminoplast condensate is mixed with fillers, e.g. cellulose or wood powder. Technical molded parts, such as housings, control knobs, electrical switches, and the like for example, are prepared from such mixtures by molding or extrusion, the aminoplast becoming cured in the process.

In the curing an extensive cross-linking takes place and this is accelerated at elevated temperatures, e.g., 100° C. or higher, by small additions of so-called curing agents or hardeners, yielding infusible, solvent-resistant products. Conventional curing agents are acid-reacting or acid-generating compounds, such as ammonium or amine salts, for example ammonium chloride, ammonium thiocyanate or ethanolaminehydrochloride.

The previously known curing agents have a series of drawbacks; e.g. the resin solutions catalyzed with the known curing agents have only short pot lives, and processing is thus considerably impaired. Also the use of known curing agents often leads to a reduction of the electrical properties so the laminated or molded articles are not suitable for use in electric fields. Some prior art curing agents effect a reduction of water fastness or by the separation of hydrogen halide, for example, corrode the processing molds or extruders.

It has now been found that maleamic and fumaramic acids and their derivatives as noted in the following formula 1, are outstandingly suitable for curing aminoplasts.

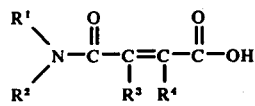

or a salt thereof
wherein $R^3$ and $R^4$ are independently hydrogen or methyl;
$R^1$ is hydrogen, or alkyl with 1 to 20 carbon atoms which may also be substituted by hydroxy, phenoxy or alkoxy with 1 to 4 carbon atoms, or phenyl or naphthyl which may be substituted by a fluorine, chlorine, bromine atom or a hydroxy group or

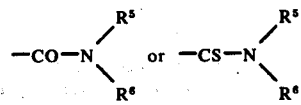

$R^5$ and $R^6$ being independently hydrogen, or alkyl with 1 to 4 carbon atoms, or hydroxyalkyl with 1 to 4 carbon atoms, or phenyl, or $R^5$ and $R^6$ together are

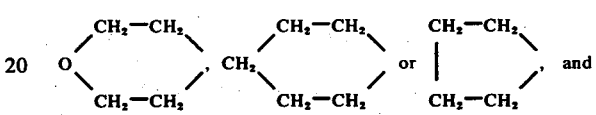

$R^2$ is hydrogen, or alkyl with 1 to 4 carbon atoms, or hydroxyalkyl with 1 to 4 carbon atoms, or $R^1$ and $R^2$ together are

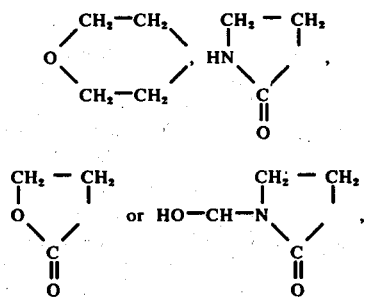

The curing agents of the present invention are normally added to the aminoplast in quantities of 0.01 to 10% by weight, and preferably 0.1 to 1% by weight.

The salt form of curing agent is a salt of the carboxyl group of Formula 1, and may contain as the cation an alkali or alkali earth metal such as lithium, sodium, potassium, magnesium or calcium as well as ammonium. Furthermore, the cation may be cationic forms of an organic amine such as an alkylamine with 1 to 4 carbon atoms, e.g. methylamine or isobutylamine, or a dialkylamine with 2 to 8 carbon atoms, e.g. dimethylamine or diisopropylamine, or a trialkylamine with 3 to 12 carbon atoms, e.g. trimethylamine or tri-n-butylamine; or aniline, morpholine, piperidine, pyrrolidine, diethanolamine or triethanolamine. Water-soluble salts are preferred.

In the compounds of the general Formula I, a cis-trans-isomerism is possible, the cis compounds being maleic acid or its derivatives and the trans compounds fumaric acid or its derivatives. For the purposes of the present invention the cis-trans isomerism is of no significance and both types of compounds are equivalent. In the preparation or use of these compounds, cis-trans rearrangements may set in but do not have to be avoided.

The compounds of Formula 1 may easily be prepared in accordance with known processes. Most simply, cyclic anhydride of Formula II is reacted with an amine or amide of Formula III.

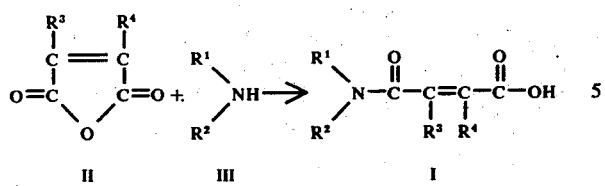

This reaction takes place spontaneously in solution in water and the resulting amide-acid usually forms with excess amine III the amine salt Ia

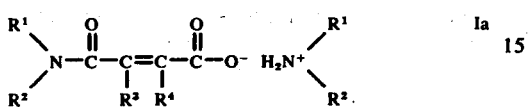

The free amide-acid may be obtained by acidifying the aqueous solution of such salt. The other salts may be easily prepared from the free acids by combining with solutions of alkali or alkaline earth hydroxides, ammonia or organic amines.

The amide-acids as well as their salts are generally old compounds and are described in *Liebig's Annalen der Chemie* 259 (1890), pages 138–139; Ber d. Deutsch. Chem. Ges. Vol. 20, page 3214, and *Journ. Org. Chem.* 25 (1960), pages 58–59. The processes there used to make these prior compounds can also be used to make new ones that fall within the present invention. Thus in place of maleic acid, pyrocinchonic acid anhydride ($R^1=R^2=H, R^3=R^4=CH_3$) or citraconic acid anhydride ($R^1=R^2=H, R^3=CH_3 R^4=H$) used as a reactant. When citraconic acid anyhdride is used the reaction product is a mixture that contains compounds with $R^3=CH_3$ and $R^4=H$ as well as compounds with $R^3=H$ and $R^4=CH_3$. However, this is unimportant for use as curing agent and both are equivalent.

Preferred curing agents of the present invention are compounds of the Formula Ib:

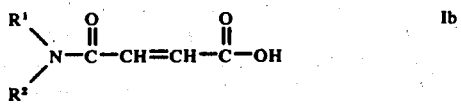

wherein
$R^1$ is hydrogen, alkyl with 1 to 4 carbon atoms or phenyl, $R^2$ is hydrogen or $R^1$ and $R^2$ together are

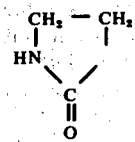

and the water-soluble salts thereof. Particularly advantageous compounds of Formula Ib are compounds Nos. 1 and 7 of the following table.

Another preferred sub-group of curing agents of the present invention have the formula Ic:

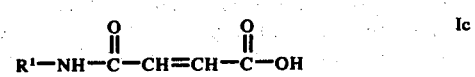

wherein

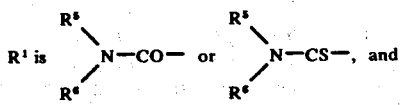

$R^5$, $R^6$ are hydrogen, methyl or ethyl, or
$R^5$ and $R^6$ together are

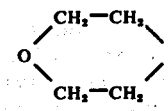

and the water-soluble salts thereof. Particularly advantageous compounds of the general formula Ic are compounds Nos. 6, 9, 11 and 21 of the following table.

The table lists typical examples of compounds having the formula given at this head, which provide very good curing action in accordance with the present invention:

TABLE $$\begin{array}{c} R^1 \\ \diagdown \\ N-C-C=CH-C-OH \\ \diagup \quad \| \quad | \quad \| \\ R^2 \quad O \quad R_3 \quad O \end{array}$$

| | $R^1$ | $R^2$ | $R^3$ | Melt. pt. in °C. | Salts |
|---|---|---|---|---|---|
| 1 | H | H | H | 190° (d) | 1,2,3,7 |
| 2 | n-C₄H₉— | H | H | | 1,2,3,12 |
| 3 | CH₂—CH₂ \ O \ CH₂—CH₂ | | H | oil | 1,2,3,13 |
| 4 | H | H | CH₃ | 139° | 1,3,8,14,15 |
| 5 | CH₃ | CH₃ | H | | 1,3,10,15 |
| 6 | S ‖ H₂N—C— | H | H | > 250° | 1,3,4,5,10 |
| 7 | CH₂—CH₂ \ HN / C ‖ O | | H | 164° | 1,2,3,4,7,8 |

TABLE-continued $$R^1\!\!\diagdown_{\phantom{N}}N-\underset{R_3}{\underset{|}{\overset{O}{\overset{\|}{C}}-\overset{\phantom{|}}{C}}}=CH-\overset{O}{\overset{\|}{C}}-OH$$
$$R^2\diagup$$

| | R¹ | R² | R³ | Melt. pt. in °C. | Salts |
|---|---|---|---|---|---|
| 8 | CH₂—CH₂ with O bridge, C=O | | H | oil | 1,2,3,5,7,8,9 |
| 9 | morpholine-N-C(=O)— | H | H | 40° | 1,2,3,4,5,6,7,11 |
| 10 | CH₃NH—C(=O)— | H | H | 186° | 1,2,3,4,5,7,10 |
| 11 | (C₂H₅)₂N—C(=O)— | H | H | 159° | 1,2,3,4,5,7,9,16 |
| 12 | HO—CH₂— | H | H | | 1,2,3,4,5,7,10,15 |
| 13 | HOCH₂—N(CH₂—CH₂)C=O | | H | | 1,2,3,4,5,10,11 |
| 14 | (HOCH₂)₂—N—C(=O)— | H | H | | 1,2,3,4,5,10,11 |
| 15 | C₆H₅— | HOCH₂— | H | | 1,2,3,4,5,11,12 |
| 16 | HOCH₂— | HOCH₂— | CH₃— | | 1,2,3,4,5,10 |
| 17 | C₄H₉— | H | H | 45° | 1,2,3,4,5,7,10 |
| 18 | C₆H₅NH—C(=O)— | H | H | 180° | 2,3,7,10 |
| 19 | p-OH═C₆H₄— | H | H | 228° | 2,3,7,10 |
| 20 | H | H | CH₃ | 139° | 2,3,4,7,10 |
| 21 | H₂N—CO— | H | H | 160° | 3,7,10,12,13 |
| 22 | C₁₈H₃₇— | H | H | 97° | 3,7,12,16 |

In the fifth column of the above table is given the melting point of the amide-acid, d meaning decomposition. Where melting point information is not given, only aqueous solutions of the amide-acid are prepared. In the last column of the above table are indicated suitable salt forms of the curing agents, the cations being:
1. sodium
2. potassium
3. ammonium
4. magnesium
5. calcium
6. barium
7. morpholinium
8. piperidinium
9. n-butylammonium
10. triethylammonium
11. diisopropylammonium
12. diethanolammonium
13. pyrrolidinium
14. anilinium
15. pyridinium The curing agents of the present invention have an outstanding latency, i.e. their addition to the aminoplast condensate reduces only slightly its pot life at room temperature in comparison to the aminoplast condensate not mixed with hardener. At elevated temperature, however, the curing agents of the present invention provide a good hardening with a satisfactorily sealed surface, and with a considerably shortened processing time, while damage to the processing tools, extruders, etc., as well as crack formations due to overhardening are not problems. In many instances the curing agents of the present invention react chemically with the aminoplast during the hardening, whereby a better resistance to water of the finished resin is achieved than if the hardener did not participate in the hardening reaction. Curing agents containing a morpholine radical or a cyclic or non-cyclic urea radical generally have a plasticizing effect when added in quantities of over 1% by weight.

According to the present invention the curing agents may be added to the aminoplast condensate in undissolved or dissolved condition. Suitable solvents are water or water-miscible organic solvents such as alcohols with 1 to 3 carbon atoms, e.g. methanol or isopropanol, ketones with 3 to 5 carbon atoms, e.g. acetone, methylethylketone; or other well-known materials such as dimethylformamide, dioxane, tetrahydrofuran, dimethylsulfoxide and the like. The preparation and further processing of the condensate take place in the usual manner.

In the following examples, the percentages given are by weight, as are the "parts". The temperatures are given in degrees Centigrade.

EXAMPLE 1

940 kg formaldehyde (39% aqueous solution)
770 kg melamine
45 kg sodium sulfamate 143 kg methanol
4 l. 2N sodium hydroxide in water
are mixed together and the mixture heated for 4 hours at 90°–95° C to cause sufficient condensation reaction to bring the water-dilutability to 1 : 2. In the determination of the water-dilutability it is found out as to how many parts by volume of water can be titrated at 20° C by one part by volume of resin without any amount of resin being deposited. To realize this procedure the resin is titrated with the aid of water. The proportion of "water-dilutability 1 : 2" as given implies that 1 ml. resin is capable of mixing up 2 ml. of water at 20° C without any turbidity occurring. The solution is then cooled, and there are added to it 150 l. water and 5.5 kg potassium salt of ethylene ureidomaleic acid of the formula

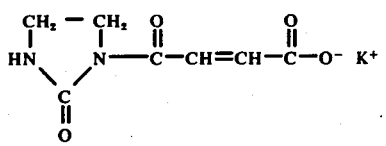

The stability of the final mixture was 5 days at room temperature. In this mixture a decorative paper weighing 110 g/m² was impregnated to a resin proportion of 45% and subsequently dried at 70° C to a residual moisture content of 5–6% as determined by weighing a sample before and after a 5-minute post-drying at 160°.

In the same solution, an overlay paper weighing 30 g/m² was also impregnated to a resin proportion of 68–72% and subsequently dried at 70° C to a residual moisture content of 6–7%.

These papers applied over 6 layers of Kraft paper impregnated with 33–37% uncured phenol-formaldehyde resin and having 6% residual moisture, except for the Kraft paper layer next to the lowest which had 1–2% higher residual moisture content (about 7%) were compressed between chromium-plated heated brass plates in a multilayer press in accordance with the following arrangement:

1 asbestos pad, 3 mm thick
1 pressing plate, chromium-plated
1 overlay paper
1 decorative paper
6 phenol papers
2 separating foils (siliconized papers)
1 pressing plate
1 asbestos pad, 3 mm thick
1 carrying plate Pressure applied: 100 Kp/cm²
Pressing temperature: 140° C
Hot pressing time: 5 minutes
Cooling time: 6 minutes The laminated material prepared showed a hardening stage of 2 according to the Kiton test. The remaining surface properties were excellent, fulfilling the requirements of DIN 16926.

The Kiton test was carried out as follows: Under a watch-glass with a 3 cm diameter, one milliliter of the following solution:

1 l. water
20 ml concentrated sulfuric acid
20 ml 2% aqueous solution of Kiton pure red 2 BL (C.I. Acid Red 45)

was allowed to act on the test surface for 2 hours. Thereafter the degree of the coloration was compared with a six-stage scale, stage 1 having no coloration
stage 6 having a strong coloration.

Stage 1 is assigned an optimum hardening and stage 6 an insufficient hardening.

In place of the potassium salt of ethylene ureidomaleic acid, the sodium, ammonium, calcium, morpholinium, piperidinium, or n-butylammonium salt of ethylene ureidomaleic acid or the sodium or potassium salt of N-(N-methylcarbamoyl)-maleamic acid can be used with similar results.

EXAMPLE 2

The procedure of Example 1 was followed but without the addition of potassium salt of ethylene ureidomaleic acid. A hot pressing time of 10 minutes was required in order to achieve the same hardening stage of the laminated material under otherwise equal conditions.

Stability of the aminoplast solution without hardener was 6 days.

EXAMPLE 3

940 kg formaldehyde (39% aqueous solution)
770 kg melamine
143 kg methanol
4 l. 2N sodium hydroxide were condensed as in Example 1 for 4 hours at 90°–95° C up to a water dilutability of 1 : 2. Subsequently there was added to the cooled solution 150 l water and 5.5 kg potassium salt of ethylene ureidomaleic acid having the formula:

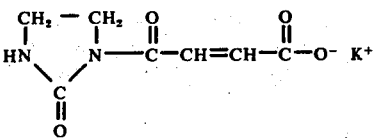

In this solution a textile fabric weighing 120 g/m² was impregnated to a resin proportion of 58–62% and dried to a residual moisture content of 5–6%. Ten layers of this impregnated fabric were laminated and compressed between heated chromium-plated nickel plates in a multilayer press.

Pressure applied: 80 Kp/cm²
Temperature: 140° C
Hot pressing time: 5 minutes
Cooling time: 6 minutes The laminated material prepared had hardening stage of 2 according to the Kiton test. The remaining surface properties satisfied the requirements of DIN 7735.

Using sodium, potassium, ammonium and morpholinium salts of maleamic acid gave the same good results.

The stability of the aminoplast solution without the curing agent was 6 days, with it 5 days. Substituting 5.5 kg of ethanolaminohydrochloride for the curing agent provided a stability of only 12 hours.

EXAMPLE 4

The procedure of Example 3 was repeated but without the addition of the potassium salt of ethylene ureidomaleic acid. A hot pressing time of 10 minutes was required in order to achieve the same hardening stage of the laminated material.

EXAMPLE 5

305 g formaldehyde (39% aqueous solution)
200 g melamine
9.5 g sorbitol, 70% in water
16 g of a mixture of equal parts of ortho and para toluene sulfonamide
16 g sugar
102 g water
2 ml 2N sodium hydroxide were condensed at 90°–95° C while maintaining the pH value of the mixture at 8.5–9.0 until the water dilution reached 1 : 1.5. To the cooled solution were added 2.0 g of the ammonium salt of N-carbamoyl maleamic acid of the formula:

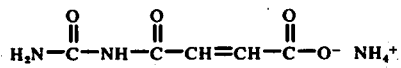

In the resulting mixture a decorative paper weighing 80g/m² was impregnated to a resin proportion of 59–61% and dried to a residual moisture content of 5–6%. This paper was placed on the upper and lower sides of a wood-chip plate having a density of 700 kg/m³ and compressed between heated chromium-plated brass plates in a multilevel press.

Hot pressing time: 6 minutes
Pressure applied 20 Kp/cm²
Temperature: 140° C
Cooling time: 5 minutes The thus cured laminate showed a high-gloss sealed surface, and its hardening corresponded to stage 2 according to the Kiton test.

When operating in accordance with Draft DIN prescriptions 68765 and 53 799, item 4.7.2 no cracks were found in the surface after the plate was stored at 70° C for 17 hours.

The stability of the aminoplast solution containing the curing agent was 8 days; without it a stability of 10 days was observed.

With the same quantity of ethanolaminohydrochloride curing agent, a stability of 24 hours was determined.

EXAMPLE 6

The procedure of Example 5 was repeated, but no curing agent was added. The final hardening obtained corresponded to stage 4–5 (severely underhardened) according to the Kiton test. The hardened surface was not sealed and in addition showed a slight adhesion to the pressing plate.

EXAMPLE 7

The procedure of Example 7 was again repeated, this time with 2 grams of ethanolaminohydrochloride added as the curing agent instead of the curing agent of Example 5. A decorative paper weighing 120 g/m² was impregnated to a resin proportion of 56–58% and dried to a residual moisture content of 5–7%. This paper was then pressed onto wood-chip plates in accordance with the procedure of Example 5.

In the examination for susceptibility to cracking, a distinct crack formation was observed on the pressed plates. The hardening corresponded to stage 2–3 according to the Kiton test.

EXAMPLE 8

500 g of a commercial pulverulent melamine-formaldehyde resin, molar ratio of melamine to formaldehyde 1:2.5
450 g powdered cellulose filler No. 402/2 B commercialized by Rettenmayer (Germany)
2 g zinc stearate
4 g titanium dioxide pigment RN 57 commercialized by Titan Co. Leverkusen (Germany)
0.5 g ammonium salt of maleamic acid of the formula

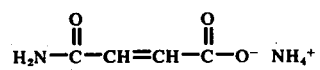

were compounded together, rolled out at 110° C on a roller frame into a rough sheet, and the rolled sheet granulated which still has a residual moisture content of about 2% (found by drying a relevant sample at 105° for half an hour). In a standard bar mold, normal bars of 120 mm × 15 mm × 10 mm according to DIN 53451 (type 152) were molded from the granulate at 155° C, an applied pressure of 250 kp/cm² and a hot pressing time of 10 minutes. The bars had the following excellent properties:

Bending strength according to DIN 53452: 940 kp/cm²
Track resistance according to DIN 53480 which denotes the maximum grade of the track resistance determined by the KA process: KA3c
Temperature stability according to DIN 53458: 126° C
Impact strength according to DIN 53453. 11.4 kp.cm/cm²
Water absorption after one-hour in boiling water, according to DIN 53472: 0.8%
Shrinkage according to DIN 53464: Height 0.8% Length 1.2%
Hardening stage (Kiton test) 2

In this instance the Kiton test is performed by immersing half of the material on test in a boiling solution of the following composition:

1 l. water
5 ml. conc. sulfonic acid
1 ml. of 2% aqueous solution of Kitonechtrot 2 BL (see C.I. Acid Red 45)

for 10 minutes.

Thereafter the grade of coloring is compared with that shown on a six-graded scale according to which grade 1 indicates no coloring
grade 6 indicates considerable coloring grade 1 is attributable to an unobjectionable cure and grade 6 to a poor cure.

EXAMPLE 9

For comparison, Example 8 was repeated, but without the addition of the ammonium salt of maleamic acid and the resulting bars had the following properties:

Bending strength according to DIN 53452: 810 kp/cm²
Track resistance according to DIN 53480: KA3c
Temperature stability according to DIN 53458: 123°
Water absorption after one-hour in boiling water according to DIN 53472: 2.3%
Shrinkage according to DIN 53464: Height 1.3% Length 2.9%
Hardening stage (Kiton test): 3–4

EXAMPLE 10

200 g melamine
320 g formaldehyde (39% aqueous solution)
4 ml 2N sodium hydroxide were condensed at 88°–92° C while the pH value of the solution held at 8.5–9.2, until it reached a water dilution of 1 : 2.0. After the addition of 100 g water and 3.2 g N-(n-butyl)-maleamic acid of the formula

it was impregnated into a fiberglass fabric weighing 120 g/m² to a resin proportion of 62–66% and the impregnated fabric dried to a residual moisture content of 6–7%.

Twelve layers of such a fabric were compressed to a laminated material in a multilayer press between heated chromium-plated brass plates, at a temperature of 130° C, a pressure of 80 kp/cm² and a hot pressing time of 20 minutes. Prior to unmolding, it was cooled to a temperature of 70°–80°. The prepared laminated material had a hardening stage of 2 according to the Kiton test. Track resistance according to DIN 53480 corresponded to the stage KA3c.

Similar good properties are obtained if in place of the free N-(n-butyl)-maleamic acid, its sodium, potassium, ammonium or diethanolammonium salts or maleic acid monomorpholide or maleamic acid are employed.

EXAMPLE 11

To a melamine aminoplast prepared according to Example 10 there was added no N-(n-butyl)-maleamic acid. Subsequent processing as in Example 10 gave a cured product having a hardening stage of 4 according to the Kiton test.

Obviously many modifications and variations of the present invention are possible in the light of the above teachings. It is therefore, to be understood that within the scope of the appended claims the invention may be practiced otherwise than as specifically described.

What is claimed is:

1. In the curing of uncured aminoplast condensation products with an acidic curing agent that under elevated temperature helps convert the condensation product to a cured resin, the improvement according to which the curing agent is

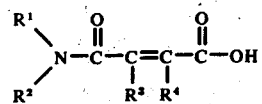

or a salt thereof
wherein
$R^3$ and $R^4$ are independently hydrogen or methyl;
$R^1$ is selected from the group consisting of hydrogen; alkyl with 1 to 20 carbon atoms which may also be substituted by hydroxy, phenoxy or alkoxy with 1 to 4 carbon atoms; phenyl or naphthyl which may be substituted by fluorine, chlorine, bromine or hydroxy;

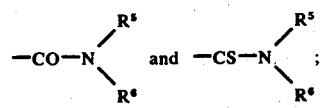

$R^5$ and $R^6$ being independently selected from the group consisting of hydrogen; alkyl with 1 to 4 carbon atoms; hydroxyalkyl with 1 to 4 carbon atoms and phenyl; or
$R^5$ and $R^6$ are selected from the group consisting of

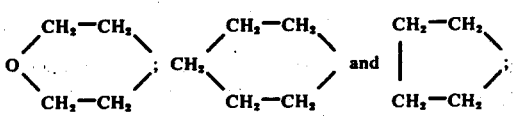

$R^2$ and is selected from the group consisting of hydrogen; alkyl with 1 to 4 carbon atoms and hydroxyalkyl with 1 to 4 carbon atoms;
$R^1$ and $R^2$ together are selected from the group consisting of

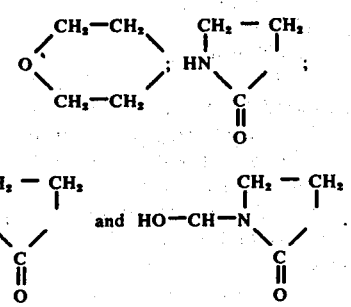

2. In an uncured aminoplast composition containing an acidic curing agent for curing at elevated temperature to a resin, the improvement according to which the curing agent is

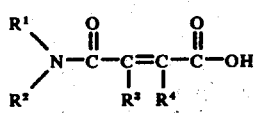

or a salt thereof
wherein
$R^3$ and $R^4$ are independently hydrogen or methyl;
$R^1$ is selected from the group consisting of hydrogen; alkyl with 1 to 20 carbon atoms which may also be substituted by hydroxy, phenoxy or alkoxy with 1 to 4 carbon atoms; phenyl or naphthyl which may be substituted by fluorine, chlorine, bromine, or hydroxy;

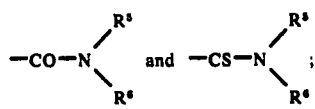

$R^5$ and $R^6$ being independently selected from the group consisting of hydrogen; alkyl with 1 to 4 carbon atoms; hydroxyalkyl with 1 to 4 carbon atoms and phenyl; or $R^5$ and $R^6$ together are selected from the group consisting of

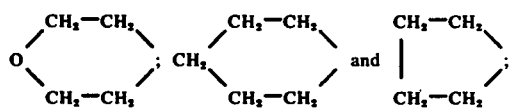

$R^2$ is selected from the group consisting of hydrogen; alkyl with 1 to 4 carbon atoms and hydroxyalkyl with 1 to 4 carbon atoms;

$R^1$ and $R^2$ together are selected from the group consisting of

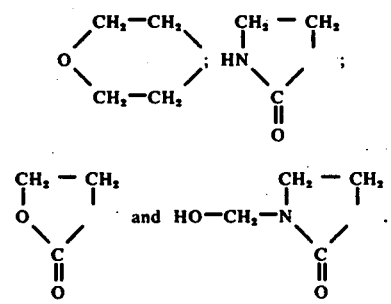

3. The combination of claim 2 in which the amount of curing agent in the composition is 0.01 to 10% by weight of the aminoplast.

4. The combination of claim 2 in which the amount of curing agent in the composition is 0.1 to 1% by weight of the aminoplast.

5. The combination of claim 2 in which $R^2$, $R^3$ and $R^4$ are hydrogen; $R^1$ is

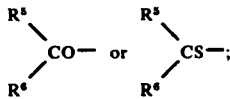

$R^5$ and $R^6$ are independently selected from the group consisting of hydrogen; methyl and ethyl; or $R^5$ and $R^6$ together are

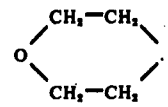

6. The combination of claim 2 in which the curing agent is maleamic acid or a water-soluble salt thereof.

7. The combination of claim 2 in which the curing agent is ethylene ureidomaleic acid or a water-soluble salt thereof.

8. The combination of claim 2 in which the curing agent is N-thiocarbamoyl maleamic acid or a water-soluble salt thereof.

9. The combination of claim 2 in which the curing agent is N-carbamoyl maleamic acid or a water-soluble salt thereof.

10. The combination of claim 2 in which the curing agent is N-(diethylcarbamoyl)-maleamic acid or a water-soluble salt thereof.

11. The combination of claim 2 in which the curing agnet is N-(morpholinocarbonyl)-maleamic acid or a water-soluble salt thereof.

12. In an uncured aminoplast composition containing an acidic curing agent for curing at elevated temperature to a resin, the improvement according to which the curing agent is

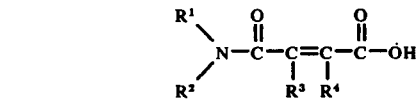

or a water-soluble salt thereof
wherein
$R^3$ and $R^4$ are independently hydrogen or methyl; and
$R^1$ is selected from the group consisting of hydrogen; alkyl with 1 to 4 carbon atoms; and phenyl; and
$R^2$ is hydrogen; or
$R^1$ and $R^2$ together are

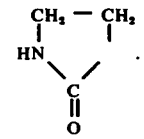

* * * * *